US008369946B2

(12) United States Patent　　(10) Patent No.: US 8,369,946 B2
Gillis et al.　　(45) Date of Patent: Feb. 5, 2013

(54) TIME BASED ARRHYTHMIA THERAPY EFFICACY CRITERIA

(75) Inventors: Anne M. Gillis, Calgary (CA); Katherine H. Anderson, Golden Valley, MN (US); Douglas A. Hettrick, Andover, MN (US); David E. Ritscher, Newton, MA (US)

(73) Assignee: Medtronic, Inc., Minneapolis, MN (US)

( * ) Notice: Subject to any disclaimer, the term of this patent is extended or adjusted under 35 U.S.C. 154(b) by 879 days.

(21) Appl. No.: 12/211,254

(22) Filed: Sep. 16, 2008

(65) Prior Publication Data

US 2010/0069982 A1　　Mar. 18, 2010

(51) Int. Cl.
*A61N 1/365*　　(2006.01)
(52) U.S. Cl. ......... 607/9; 607/1; 607/2; 607/14; 607/25; 607/115; 607/116; 607/119; 600/508; 600/509; 600/510; 600/515
(58) Field of Classification Search .................. 607/1–2, 607/9, 14, 25, 115–116, 119; 600/508–510, 600/515
See application file for complete search history.

(56) References Cited

U.S. PATENT DOCUMENTS

| | | | |
|---|---|---|---|
| 7,167,743 B2 | 1/2007 | Heruth et al. | |
| 7,212,855 B1 | 5/2007 | Kroll et al. | |
| 7,225,020 B1 | 5/2007 | Kroll et al. | |
| 7,308,308 B1 | 12/2007 | Xi et al. | |
| 2004/0077995 A1 | 4/2004 | Ferek-Petric et al. | |
| 2004/0167579 A1 | 8/2004 | Sharma et al. | |
| 2006/0074331 A1* | 4/2006 | Kim et al. | 600/515 |
| 2006/0241722 A1 | 10/2006 | Thacker et al. | |
| 2007/0043393 A1 | 2/2007 | Brockway et al. | |
| 2007/0150011 A1 | 6/2007 | Meyer et al. | |
| 2007/0213773 A1 | 9/2007 | Hill et al. | |
| 2007/0276439 A1 | 11/2007 | Miesel et al. | |

OTHER PUBLICATIONS

Anne M. Gillis, et al., "Safety and Efficacy of Advanced Atrial Pacing Therapies for Atrial Tachyarrhythmias in Patients with a New Implantable Dual Chamber Cardioverter-Defibrillator", Journal of the American College of Cardiology, vol. 40., No. 9, Nov. 6, 2002, pp. 1653-1659.
Dirk Vollmann, et al., "Automatic Atrial Anti-Tachy Pacing for the Termination of Spontaneous Atrial Tachyarrhythmias; Clinical Experience with a Novel Dual-Chamber Pacemaker", Journal of Interventional Cardiac Electrophysiology, vol. 5, No. 4, Dec. 2001, pp. 477-485.
B. Hügl et al., "Incremental Programming of Atrial Anti-Tachycardia Pacing Therapies in Bradycardia-indicated Patients: Effects on Therapy Efficacy and Atrial Tachyarrhythmia Burden", The European Society of Cardiology, vol. 5, No. 4, Oct. 1, 2003, pp. 403-409.
Dirk Vollmann et al., "Comparison of Immediate and Delayed Automatic Antitachycardia Pacing for the Termination of Atrial Tachyarrhythmias", The European Society of Cardiology, vol. 7, No. 3, Apr. 19, 2005, pp. 248-254.
(PCT/US2009/056327) PCT Notification of Transmittal of the International Search Report and the Written Opinion of the International Searching Authority, 14 pages.

* cited by examiner

*Primary Examiner* — Carl H Layno
*Assistant Examiner* — Deborah Malamud
(74) *Attorney, Agent, or Firm* — Michael C. Soldner

(57) ABSTRACT

An implantable medical device and associated method classify therapy outcomes and heart rhythms in association with therapy outcome. A therapy success time interval is started in response to delivering an arrhythmia therapy. If normal sinus rhythm is detected after the therapy success time interval expires, the delivered therapy is classified as unsuccessful and the detected arrhythmia is classified as a self-terminating rhythm.

12 Claims, 3 Drawing Sheets

TIME BASED ARRHYTHMIA THERAPY EFFICACY CRITERIA

TECHNICAL FIELD

The present discloser relates generally to implantable medical devices and, in particular, to implantable cardiac stimulation devices and methods for determining efficacy of a cardiac stimulation therapy.

BACKGROUND

In implantable cardioverter defibrillators (ICDs) used to treat cardiac arrhythmias, a cardiac arrhythmia therapy is automatically classified by the ICD as successful if normal sinus rhythm (NSR) is detected after therapy delivery. Conversely, the therapy may be declared unsuccessful if the arrhythmia is re-detected following completion of the therapy. However, in some cases, the normal sinus rhythm may occur later than an effective time period for the therapy. A heart rhythm may remain unclassified after therapy delivery during a period of time in which detection criteria for detecting normal sinus rhythm and detection criteria for redetecting an arrhythmia both remain unmet. An eventual NSR classification may result in the therapy outcome being classified as successful even though the restored NSR occurred later than the expected effective time period of the therapy. Such a successful therapy outcome classification overestimates the therapy success rate since the return to sinus rhythm is more likely representative of a self-terminating arrhythmia then the result of an effective therapy.

DETAILED DESCRIPTION

Figure 1:
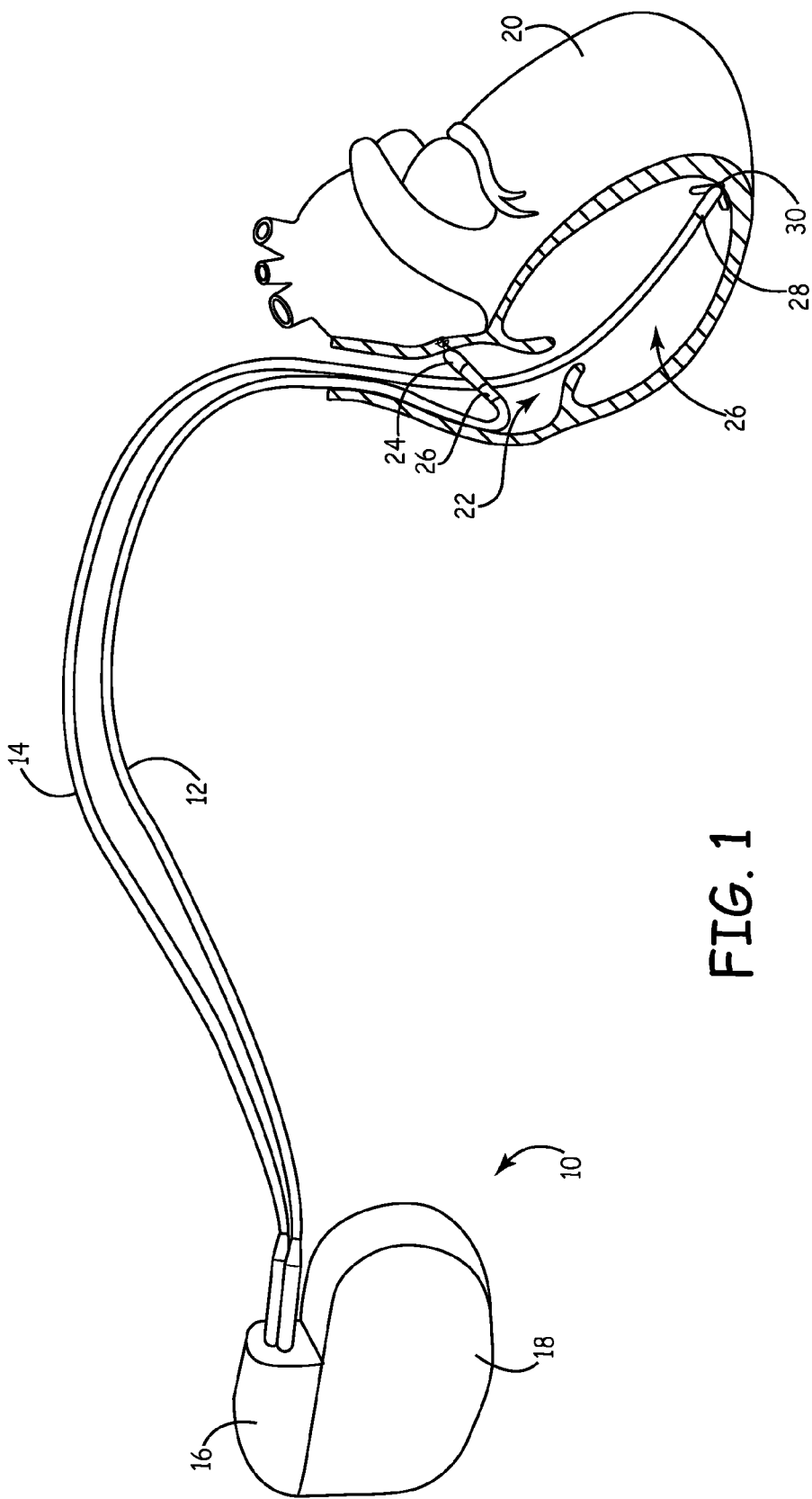
FIG. 1 provides a schematic view of one embodiment of an IMD in which methods described herein for classifying a heart rhythm may be implemented.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 provides a schematic view of one embodiment of an IMD 10 that can be adapted to perform methods described herein for classifying a heart rhythm. In accordance with one embodiment of the invention, IMD 10 can be configured to apply arrhythmia therapies to one or both atria following detection of an arrhythmia episode. In particular, IMD 10 is programmed to automatically deliver atrial arrhythmia therapies, such as overdrive pacing or cardioversion pulses, upon detecting an arrhythmia. The IMD 10 is embodied as a cardiac pacemaker or implantable cardioverter-defibrillator (ICD) including pacing and sensing leads 12, 14 coupled to a connector module 16 of a hermetically sealed enclosure 18 and implanted near a heart 20 of a subject. Pacing and sensing leads 12, 14 sense electrical signals attendant to the depolarization and repolarization of the heart 20, and further provide stimulation pulses for causing depolarization of cardiac tissue in the vicinity of the distal ends of the leads as needed.

Atrial pacing and sensing lead 12 extends from connector module 16 to the right atrium 22 of heart 20 and may alternatively extend to the left atrium. At least one pair of atrial electrodes 24, 26 are disposed in communication with an atrial chamber (e.g., as depicted, right atrium 22) at the distal end of atrial lead 12. IMD 10 may include ventricular sensing and therapy delivery functions and is thus shown provided with ventricular pacing and sensing lead 14 extending from connector module 16 to the right ventricle 26 of heart 20. Ventricular electrodes 28, 30 are disposed in right ventricle 26 at the distal end of ventricular lead 14. Leads 12, 14 may carry one or more electrodes for use in unipolar, bipolar or multipolar configurations. Ventricular electrodes may additionally or alternatively be placed in operative relation to the left ventricle.

IMD 10 can deliver cardiac pacing therapy to a ventricle 26 via electrodes 28, 30. IMD 10 can coordinate ventricular pacing with atrial activity sensed via atrial electrodes 24, 26 during atrial tracking pacing modes. Atrial electrodes 24, 26 can also be employed to sense an atrial tachyarrhythmia such as fibrillation or flutter (AF), and to administer therapy, such as overdrive pacing. IMD 10 is configured to switch pacing modes to a non-atrial tracking mode upon detection of AF. While lead-based intra-cardiac electrodes are shown in FIG. 1, it is recognized that IMD systems implementing embodiments of the present invention may include leadless (housing-based) electrodes and subcutaneous electrodes carried by subcutaneous leads.

Embodiments are directed to correctly classifying atrial rhythms and the success of atrial arrhythmia therapies. In particular, atrial arrhythmias determined to self-terminate after delivery of an atrial arrhythmia therapy are distinguished from atrial arrhythmias that terminate due to therapy delivery. In past practice, after an arrhythmia therapy is delivered, the heart rhythm is monitored until normal sinus rhythm is detected or until an arrhythmia is redetected. If an arrhythmia is redetected, the arrhythmia therapy is classified as unsuccessful. The therapy may be repeated or another therapy may be selected and delivered. If normal sinus rhythm is detected, the delivered therapy is classified as successful. The outcome classification may be made based on the arrhythmia not being redetected within a predefined time interval, for example three minutes, following the therapy delivery. An arrhythmia detected after three minutes would be detected as a new arrhythmia episode.

However, in some circumstances, neither normal sinus rhythm detection criteria nor arrhythmia detection criteria may be satisfied for a period of time following therapy delivery. For example, a long period of sinus rhythm with intermittent premature atrial contractions may fail classification as either NSR or atrial tachycardia or atrial fibrillation based on sensed cardiac event interval criteria. Furthermore, normal sinus rhythm may be detected one or two minutes following the therapy delivery, after the period of time within which the therapy is expected to be effective. In past practice, the NSR detection would result in a successful therapy outcome classification. However, the delayed return to NSR after therapy delivery is more likely representative of a self-terminating rhythm than a successful therapy. Accordingly, embodiments of the present invention address the classification of rhythms that self-terminate after therapy delivery and distinguish such rhythms from rhythms that terminate in response to a successful therapy. This distinction can provide a more accurate representation of the efficacy of device therapies to the clinician monitoring the device performance and managing the patient therapies.

Figure 2:
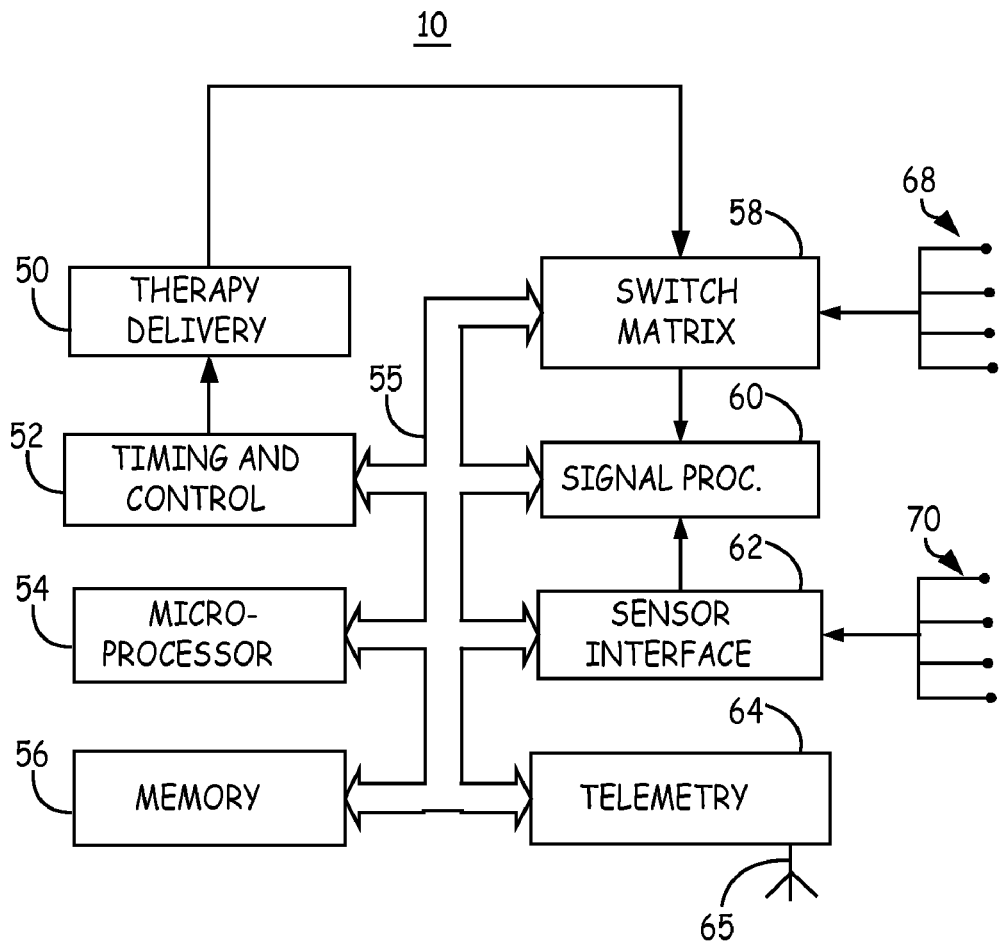
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55. IMD 10 includes therapy delivery module 50 for delivering a therapy in response to determining a need for therapy based on sensed physiological signals. Therapy delivery module 50 may provide drug delivery therapies or electrical stimulation therapies, such as cardiac pacing or arrhythmia therapies. Therapies are delivered by module 50 under the control of timing and control 52. Therapy delivery module 50 is typically coupled to two or more electrode terminals 68 via an optional switch matrix 58. Switch matrix 58 may be used for selecting which electrodes and corresponding polarities are used for delivering electrical stimulation pulses, such as electrodes 24, 26, 28 and 30 shown in FIG. 1.

Electrode terminals 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. Microprocessor 54 may further execute algorithms for detecting and classifying the outcome of delivered therapies in association with cardiac rhythms classified following the delivery of therapy.

IMD 10 may additionally be coupled to one or more physiological sensors via physiological sensor terminals 70. Physiological sensors may include pressure sensors, accelerometers, flow sensors, blood chemistry sensors, activity sensors or other physiological sensors known for use with implantable devices. Physiological sensors may be carried by leads extending from IMD 10 or incorporated in or on the IMD housing 18.

Signals received at sensor terminals 70 are received by a sensor interface 62 which provides sensor signals to signal processing circuitry 60. Sensor signals are used by microprocessor 54 for detecting physiological events or conditions and may be stored for use in diagnosing or monitoring the patient or used in determining the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 may be used for storing the classification of therapy outcomes and heart rhythms for analysis by the device and/or review by a clinician. According to embodiments of the present invention, unsuccessful therapy outcome classifications are discriminated between ongoing arrhythmias that did not terminate in response to the delivered therapy, i.e. the arrhythmia is redetected, and self-terminating arrhythmias that did not respond to the delivered therapy but spontaneously terminated subsequent to the therapy delivery. In past practice, any therapy that did not result in arrhythmia redetection was classified as a successful therapy. The overall therapy success rate may be over-estimated due to self-terminating rhythms being counted among the arrhythmia episodes that were successfully terminated by a therapy. As such, memory 56 may include a log or histogram of therapy outcome and rhythm classifications that identifies self-terminating rhythm classifications associated with unsuccessful therapy outcomes.

IMD 10 further includes telemetry circuitry 64 and antenna 65. Programming commands or data are transmitted during uplink or downlink telemetry between ICD telemetry circuitry 64 and external telemetry circuitry included in a programmer or monitoring unit. Telemetry circuitry 64 and antenna 65 may correspond to telemetry systems known in the art.

Figure 3:
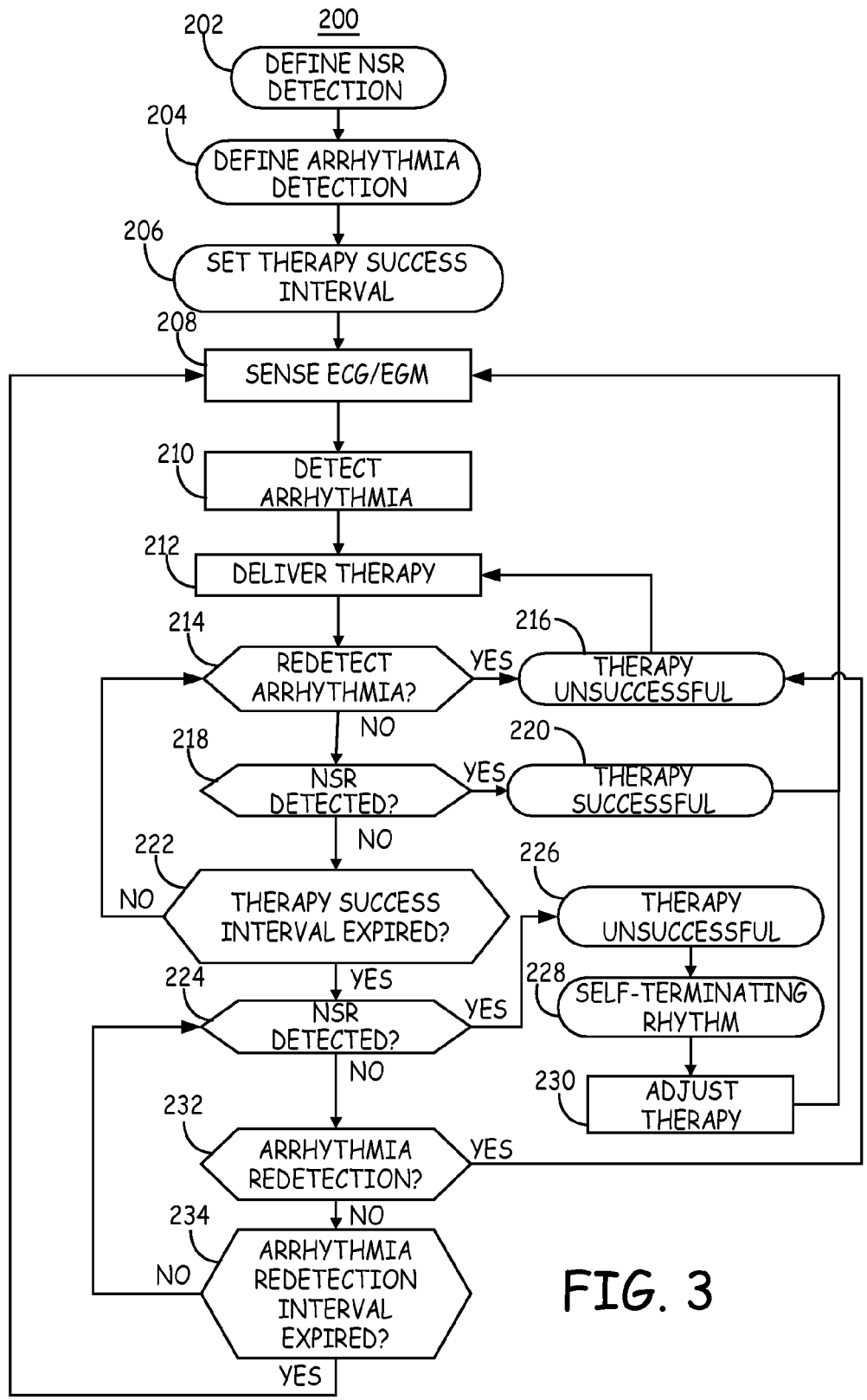
FIG. 3 is a flow chart of a method for classifying therapy outcomes and heart rhythms according to one embodiment of the invention.

FIG. 3 is a flow chart 200 of a method for classifying therapy outcomes and heart rhythms according to one embodiment of the invention. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, detection criteria for detecting normal sinus rhythm (NSR) after detecting any arrhythmia or delivering an arrhythmia therapy are defined and stored. In one embodiment, NSR is detected after detecting a predetermined number of consecutive cardiac cycles, i.e. R-R intervals, that are longer than a maximum tachycardia detection interval. For example, NSR detection criteria may be defined as five consecutive R-R intervals longer than a user defined limit for arrhythmic intervals. NSR detection criteria may be predefined and stored in the IMD or may be programmable by a clinician.

At block 204, arrhythmia detection criteria are defined and stored. Arrhythmia detection criteria typically include detecting N out of M cardiac cycles shorter than a tachycardia detection interval. Arrhythmia detection criteria may include multiple rate zones based on different detection interval ranges for discriminating slow tachycardia, fast tachycardia and fibrillation. Arrhythmia detection criteria are typically programmable and, though not shown explicitly in FIG. 3, may include different sets of criteria for detecting a new arrhythmia episode and for re-detecting an arrhythmia episode after delivering a therapy.

At block 206, a time interval is set within which a therapy outcome can be classified as successful. As will be further described below, if a therapy is delivered, the therapy outcome is classified as successful only when NSR is detected prior to the expiration of the therapy success interval. NSR detected after this predefined time interval results in an unsuccessful therapy outcome classification and a self-terminating rhythm classification. The therapy success interval may be programmable and may be tailored to the particular therapy delivered and to a particular patient's needs. In embodiments that include different therapies available for delivery depending on the arrhythmia being treated, the therapy success interval may be defined uniquely for each of the different therapies. In one embodiment, the therapy success interval is programmable in seconds up to a maximum interval of 60 seconds.

At block 208, the EGM/ECG signal is sensed. Sensed signals used for detecting heart rhythm may include an intracardiac EGM signal using transvenous leads and/or ECG signals acquired using subcutaneous or submuscular electrodes, which may be lead-based or IMD housing based electrodes.

At block 210, an arrhythmia is detected using the sensed ECG/EGM signal according to the arrhythmia detection criteria. A therapy is delivered in response to the arrhythmia detection at block 212. A delivered therapy is typically programmable. Therapies may be programmed to include a menu of tiered therapies beginning with a least aggressive therapy and progressing to more aggressive therapies, such as a shock pulse, when an arrhythmia is redetected after an unsuccessful therapy. The delivered therapy may include electrical stimulation therapies, such as overdrive pacing, a burst of high frequency pacing pulses, or a cardioversion/defibrillation shock. Delivered therapies may additionally or alternatively include drug therapies. The predefined successful therapy detection time interval is defined in accordance with the time frame a particular therapy would be expected to take effect if successful. For an electrical stimulation therapy this time frame is generally less than one minute and may be as short as several seconds. For drug therapies this time frame may be longer.

Prior to the expiration of the therapy success interval, if an arrhythmia is redetected, at block 214, the therapy outcome is classified as unsuccessful at block 216. A therapy may be redelivered or an adjusted or new therapy may be delivered according to the programmed therapies by returning to block 212. If NSR is detected at block 218, prior to expiration of the therapy success interval, the therapy outcome is classified as successful at block 220. ECG/EGM monitoring continues by returning to block 208.

After expiration of the therapy success interval at block 222, a NSR detection at block 224 no longer results in a successful therapy outcome classification. Unlike past practice, in which a NSR detection after arrhythmia therapy without an intervening arrhythmia detection resulted in a successful therapy outcome classification, the NSR detection occurring after the therapy success interval is determined to be the result of a self-terminating rhythm and not due to the therapy delivery. The restoration of NSR occurring after the therapy success interval is assumed to be too late to be the result of the therapy. Accordingly, the therapy outcome is classified as unsuccessful at block 226 and the rhythm is classified as a self-terminating rhythm at block 228.

This self-terminating rhythm classification may be used to adjust therapy settings at block 230. For example, if a number of arrhythmia episodes are classified as self-terminating rhythms, arrhythmia therapies may be turned off to allow future arrhythmias of the same type to self-terminate without therapy delivery. Alternatively, the therapy may be adjusted to treat the arrhythmia more aggressively or otherwise increase the likelihood of therapy success in order to terminate the arrhythmia more quickly and reduce the overall arrhythmia burden.

If NSR is not detected after the therapy success interval and the arrhythmia is redetected at block 232, the therapy outcome is classified as unsuccessful at block 216 and a next therapy may be delivered at block 212. Typically a time interval is set during which an arrhythmia detection is considered a redetection of the same arrhythmia episode. As such, any arrhythmia redetected at block 232 may trigger the next therapy in a menu of tiered therapies. If the arrhythmia redetection interval has expired, at block 234, the ECG/EGM signal continues to be monitored at block 208 and any arrhythmia detection occurring thereafter at block 210 is considered a new arrhythmia episode. The arrhythmia re-detection interval may be about three minutes but may be as short as 1 minute or as long as five minutes in some embodiments. Embodiments of the invention are not limited to any specific therapy success interval or arrhythmia redetection interval and these intervals may be made programmable by a clinician.

In the rare occurrences that neither NSR detection nor arrhythmia redetection occurs during the arrhythmia redetection interval, though not explicitly shown in FIG. 3, an eventual NSR detection would still result in an unsuccessful therapy outcome classification and self-terminating rhythm classification. In the event of an eventual new arrhythmia episode detection with no intervening NSR detection, the therapy outcome would be classified as unsuccessful with the intervening rhythm classification being undefined.

The predefined therapy success interval allows discrimination between rhythms that terminate within an effective time frame of the therapy and those rhythms that self-terminate after the therapy but later than the expected efficacy of the therapy. By separately classifying self-terminating rhythms that are unsuccessfully treated by a therapy from rhythms successfully treated by a therapy, a clinician can better evaluate the overall effectiveness of the therapy and the therapy response and need in individual patients.

Thus, an implantable medical device system and associated method for classifying heart rhythm and therapy outcomes have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device, comprising:
    setting a first predetermined time interval for use in classifying a therapy outcome;
    sensing cardiac electrical signals for determining a heart rhythm;
    detecting an arrhythmia in response to the cardiac electrical signals;
    delivering an arrhythmia therapy in response to detecting the arrhythmia;
    starting the first predetermined time interval in response to delivering the therapy;
    determining if normal sinus rhythm is detected after expiration of the first predetermined time interval;
    classifying the delivered therapy as unsuccessful in response to the normal sinus rhythm detection occurring after expiration of the first predetermined time interval; and classifying the detected arrhythmia as a self-terminating rhythm in response to the normal sinus rhythm detection occurring after the first predetermined time interval.

2. The method of claim 1 wherein the arrhythmia being an atrial arrhythmia.

3. The method of claim 2 wherein the therapy is adjusted in response to the self-terminating rhythm classification.

4. The method of claim 3 further comprising:
defining a second time interval longer than the first time interval;
starting the second time interval in response to the therapy delivery;
detecting an arrhythmia during the second time interval; and
classifying the therapy as unsuccessful in response to the arrhythmia being detected during the second time interval.

5. The method of claim 1 further comprising classifying the therapy outcome as unsuccessful in response to neither of a normal sinus rhythm and an arrhythmia being detected during the predetermined time interval.

6. The method of claim 1 further comprising storing the self-terminating rhythm classification in association with the unsuccessful therapy outcome classification in memory.

7. An implantable medical device system, comprising:
means for setting a first predetermined time interval for use in classifying a therapy outcome;
means for determining a heart rhythm;
means for delivering an arrhythmia therapy in response to detecting the arrhythmia;
a processor configured to start the predetermined time interval in response to delivering the therapy and for determining if normal sinus rhythm is detected after expiration of the predetermined time interval, classifying the delivered therapy as unsuccessful in response to the normal sinus rhythm detection occurring after expiration of the predetermined time interval, and classifying the detected arrhythmia as a self-terminating rhythm in response to the normal sinus rhythm detection occurring after the predetermined time interval; and
memory for storing the unsuccessful therapy outcome classification in association with the self-terminating rhythm classification.

8. The system of claim 7 wherein the arrhythmia being an atrial arrhythmia.

9. The system of claim 7 wherein the processor being further configured to adjust the therapy in response to the self-terminating rhythm classification.

10. The system of claim 9 further comprising:
means for setting a second time interval longer than the first time interval;
wherein the processor further configured to start the second time interval in response to the therapy delivery, detect an arrhythmia during the second time interval, and classify the therapy as unsuccessful in response to the arrhythmia being detected during the second time interval.

11. The system of claim 7 wherein the processor further configured to classify the therapy outcome as unsuccessful in response to neither of a normal sinus rhythm and an arrhythmia being detected during the first predetermined time interval.

12. A non-transitory computer readable medium storing a set of instructions which when implemented in an implantable medical device system cause the system to:
set a predetermined time interval for use in classifying a therapy outcome;
sense cardiac electrical signals for determining a heart rhythm;
detect an arrhythmia in response to the cardiac electrical signals;
deliver an arrhythmia therapy in response to detecting the arrhythmia;
start the predetermined time interval in response to delivering the therapy;
determine if normal sinus rhythm is detected after expiration of the predetermined time interval;
classify the delivered therapy as unsuccessful in response to the normal sinus rhythm detection occurring after expiration of the predetermined time interval; and
classify the detected arrhythmia as a self-terminating rhythm in response to the normal sinus rhythm detection occurring after the predetermined time interval.

\* \* \* \* \*